United States Patent [19]
Kebabian

[11] Patent Number: 5,818,598
[45] Date of Patent: Oct. 6, 1998

[54] NONDISPERSIVE OPTICAL MONITOR FOR NITROGEN-OXYGEN COMPOUNDS

[75] Inventor: Paul Kebabian, Acton, Mass.

[73] Assignee: Aerodyne Research, Inc., Billerica, Mass.

[21] Appl. No.: 770,432

[22] Filed: Dec. 20, 1996

[51] Int. Cl.$^6$ ................................................ G01N 21/61
[52] U.S. Cl. ............................................ 356/434; 356/437
[58] Field of Search .................................. 356/435, 437, 356/438, 439, 414; 250/339.13, 345

[56] References Cited

U.S. PATENT DOCUMENTS

| | | |
|---|---|---|
| 2,389,046 | 11/1945 | Hare . |
| 3,103,586 | 9/1963 | Ovrebo et al. ........................ 250/345 |
| 3,718,429 | 2/1973 | Williamson, Jr. . |
| 3,811,776 | 5/1974 | Blau, Jr. ................................. 356/51 |
| 3,860,818 | 1/1975 | Stadler et al. ......................... 250/343 |
| 4,272,249 | 6/1981 | D'Antonio ............................. 23/232 |
| 4,632,563 | 12/1986 | Lord ...................................... 356/437 |

OTHER PUBLICATIONS

Herget et al., *Applied Optics*, 15:1222–1228 (May 1976).

*Primary Examiner*—Richard A. Rosenberger
*Attorney, Agent, or Firm*—Cesari and McKenna, LLP

[57] ABSTRACT

A gas-correlation filter spectroscopy-based method and apparatus for determining the concentration of gas species having significant average broadband absorption incorporates a compensating filter having an absorption spectrum that varies with wavelength similarly to the spectrum of the gas species. The compensating filter eliminates interference due to differential absorption. The invention is especially suited to detecting nitrogen dioxide.

49 Claims, 2 Drawing Sheets

NONDISPERSIVE OPTICAL MONITOR FOR NITROGEN-OXYGEN COMPOUNDS

This invention was made with government support under United States Environmental Protection Agency contract no. 68D50105. The government has certain rights in this invention.

FIELD OF THE INVENTION

This invention relates generally to optical sensors. More particularly, this invention relates to methods and apparatus for measuring the concentration of nitrogen dioxide or other compounds of nitrogen and oxygen in an environment of interest.

BACKGROUND OF THE INVENTION

Nitric oxide ("NO") and nitrogen dioxide ("$NO_2$"), collectively called $NO_x$, contribute to urban ozone formation, photochemical smog, and acid rain. These gases are emitted chiefly as byproducts of combustion, for example by large stationary sources such as power plants. Flue gas from such sources typically contains 100 parts-per-million to 1000 parts-per-million $NO_x$, most of which is NO. Thus, a sensitivity in the 1-ppm range is appropriate for monitoring such effluent compositions, for example as part of a scrubber control system. In addition to air pollution control applications, $NO_x$ detection is useful for monitoring and control of indoor air quality, particularly in workplace environments in which chemical processes that may produce $NO_x$ are in use.

Currently, the predominant method of measuring $NO_x$ requires first reducing the $NO_2$ to NO using a heated molybdenum catalyst and then measuring total $NO_x$ using the chemiluminescent reaction of NO with ozone. This approach entails a relatively complex and expensive analyzer apparatus which has several drawbacks. In particular, such analyzers require a cooled photomultiplier tube to detect the faint, near-infrared light emitted by the ozone reaction. The photomultiplier tube and its thermoelectrically cooled housing significantly increase the cost of the analyzer. Furthermore, the analyzer requires a vacuum pump to provide the low-pressure environment conducive to the ozone reaction. The necessity for several sensitive parts decreases the reliability of the system. Finally, such chemiluminescent analyzers are sensitive at the parts-per-billion range, far below the levels relevant to combustion source monitoring.

Another chemiluminescent technique oxidizes any NO in the sample and then uses luminol to detect $NO_2$; this technique requires regular replenishment of a liquid reagent. Systems relying on electrochemical cells have a limited lifetime, due in part to their use of a liquid electrolyte. Finally, approaches based on absorption of laser light, extremely expensive and complex, require a skilled operator.

DESCRIPTION OF THE INVENTION

Objects of the Invention

An object of the present invention is, accordingly, a gas species detector that is simple, reliable and inexpensive to build and operate.

Another object of the invention is a nitrogen dioxide detector operable at ambient pressure.

Another object of the invention is a nitrogen dioxide detector that uses no liquid reagent.

Yet another object of the invention is a nitrogen dioxide detector sensitive to nitrogen dioxide concentrations in the 100-to-1000 parts-per-million range.

Brief Summary of the Invention

The invention provides a detector based on nondispersive gas filter correlation spectroscopy ("GFCS") for a gas species having significant broadband average absorption. (See, e.g., Herget et al. "Infrared Gas-Filter Correlation Instrument for In Situ Measurement of Gaseous Pollutant Concentrations", Applied Optics, 15, 1222–28 1976.) Gas filter correlation spectroscopy exploits the correlation between the highly characteristic structure of the absorption spectrum of a gas species of interest in the sample and that of a correlation filter—a cell containing the same gas species. Radiation including several characteristic wavelengths strongly absorbed by the species of interest alternately passes through or bypasses the correlation filter—typically effected in prior art systems by mechanically interposing the correlation filter periodically into and out of the optical pathway—and then through the sample. Ideally, the optical density of the gas in the correlation filter is sufficient so that the correlation filter completely removes wavelengths characteristic of the species of interest before the light interacts with that species in the sample, so that the sample does not further change the total intensity of the light filtered by the correlation filter. On the other hand, the sample strongly absorbs light that has bypassed the correlation filter at wavelengths characteristic of the gas species. Thus, comparison of the sample's absorption of light that has first passed through the correlation filter and its absorption of light that has bypassed the correlation filter indicates the concentration of the species of interest in the sample. If the intensity of the light that has bypassed the filter is adjusted to match the intensity of light filtered by the correlation filter, for example by a neutral density filter or attenuator, the concentration may be derived directly from the difference between the intensities of light from the two filters leaving the sample compared with calibration data.

In the detector of the invention, light passes through the sample after passing alternately through the correlation filter and a compensating filter. The compensating filter is characterized by an average transmission having a wavelength dependence that approximately matches that of the correlation filter, without the characteristic spectral lines. Light leaving the compensating filter retains significant intensity at the strongly absorbed characteristic wavelengths, which is then decreased by interaction with the sample. Thus, the comparison of the sample's absorption of light processed by the two filters indicates the concentration of the species of interest in the sample.

The presence of the compensating filter overcomes the limitations of prior-art infrared ("IR") GFCS vis-à-vis absorption by a gas species whose absorption spectrum has significant broadband average absorption—in general wavelength-dependent—in addition to characteristic lines. Nitrogen dioxide and several of the halogens have such spectra. For example, the visible light absorption spectrum of nitrogen dioxide from 450 to 550 nm as shown by the dashed curve in FIG. 1 comprises bands of lines that are not resolvable on the scale of the figure [based on measurements of Corcoran et al, *J. Molecular Spectroscopy* 154, 119–128 (1992)]. Substantial overlap among the very large number of lines creates significant wavelength-dependent average absorption, indicated in the figure by the solid line.

The spectral variation of the average absorption is much less species-specific than the spectral lines. Correlation between the average absorption of a species of interest and that of a gaseous interferent species also having significant broadband absorption may exist even if the narrow spectral features of the two species show no correlation. In the absence of a compensating filter, such an interferent species will produce a spurious signal indicating the presence of the species of interest. Particulate scatterers such as smoke or dust, or contaminants like oil, in the optical path can cause similar interference. Such broadband interference severely limits the utility of GFCS for detecting species like $NO_2$ having wavelength-dependent average absorption and a large relevant observation bandwidth.

The invention eliminates these difficulties by including a compensating filter that matches the spectral dependence of the average transmission by the correlation filter. (Note that the optical thickness, equal to the logarithm of the reciprocal of the transmission, of the compensating filter approximately follows the average absorption cross-section; however, at any given wavelength light is attenuated exponentially by the gas in the correlation filter, so that matching the form of the average transmission of the correlation and compensating filters is comparable but not strictly identical to matching the form of their average absorption cross-sections.) The difference in absorption between the path through the correlation filter and that path through the compensating filter is independent of wavelength when averaged over a spectral resolution that is large compared to the species' individual line widths but small compared to the total observation bandwidth. Thus, wavelength-dependent broadband absorption does not spuriously contribute to the indication of interest.

For gases showing such average broadband absorption underlying narrow absorption features in the visible part of the spectrum, the invention provides a GFCS detector that exploits visible light sources, which are more powerful and less expensive than IR sources. The affordability and reliability of the invention is especially enhanced when light-emitting diodes ("LEDs"), which offer high efficiency, good output stability and long lifetime, are used for the light source. Furthermore, LEDs respond quickly enough so that they can be switched electronically at any rate required for practical gas species detection. This feature makes possible a dual-optical path configuration in which an LED is dedicated to each of the filters. This configuration eliminates the necessity for a mechanism that moves the filters into and out of the optical pathway of a single light source, thereby reducing the mechanical complexity of the GFCS detector. In a preferred embodiment, the invention provides a $NO_2$ detector that uses light from LEDs that emit in the 400-to-550 nm spectral region, most preferably of indium-gallium nitride.

The compensating filter may be of a glass incorporating ionic additives that conform the absorption properties of the glass to the average absorption of the gas species. In a preferred embodiment, the invention provides a $NO_2$ detector having a compensating filter having the composition of FG-13 filter glass, made by Schott Glass Technologies of Duryea, Pa. In another preferred embodiment, the compensating filter is a cell containing $NO_2$ under conditions identical to those in the correlation filter, except that it is situated in a magnetic field having field strength of on the order of several thousand Gauss. Zeeman splitting of some of the absorption lines of nitrogen dioxide, by an amount comparable to their width, is sufficient to partially decorrelate their narrow spectral features from those of the $NO_2$ in the correlation filter while leaving the average absorption virtually unchanged.

In another aspect, the invention provides a $NO_x$ detector that functions by first converting NO to $NO_2$ and then measuring the total $NO_2$ in the product. The oxidation of NO is preferably performed by exposing the sample to ozone, generated in situ.

In yet another aspect, the $NO_2$ detector of the invention is adapted to function as a highly sensitive temperature sensor based on the temperature-dependent equilibrium between the monomeric and dimeric forms of $NO_2$. Such a sensor comprises a sealed vessel containing about 40 to 100 Torr of pure $NO_2$ functioning as the sample. The amount of the $NO_2$ in the transparent dimeric form increases with decreasing temperature, and the signal indicative of monomeric $NO_2$ decreases. Around normal ambient temperatures, the temperature dependence of measured $NO_2$ is steep and nearly linear.

The temperature sensor of the invention may be used to advantage whenever near-ambient temperatures must be measured accurately from a remote position, since the sealed vessel may be connected to the monitoring elements by optical fibers of up to tens of meters in length, limited only the optical losses in the fibers. Such applications include, for example, remote meteorological stations, where there is a risk of damage to electrical sensors by lightning, and electrical power machinery such as transformers or thyristor stacks, where the sensor may be located at a high electrical potential.

Thus, in one or more of its embodiments the invention provides a GFCS-based device, suitable for measuring gases having a visible light absorption spectrum comprising narrow absorption lines, even in the presence of underlying broadband absorption, requiring minimal moving parts.

BRIEF DESCRIPTION OF THE DRAWINGS

The foregoing discussion will be understood more readily from the following detailed description of the invention, when taken in conjunction with the accompanying drawings, in which like reference numerals indicate identical or functionally similar elements.

DETAILED DESCRIPTION OF THE INVENTION

Figure 1:
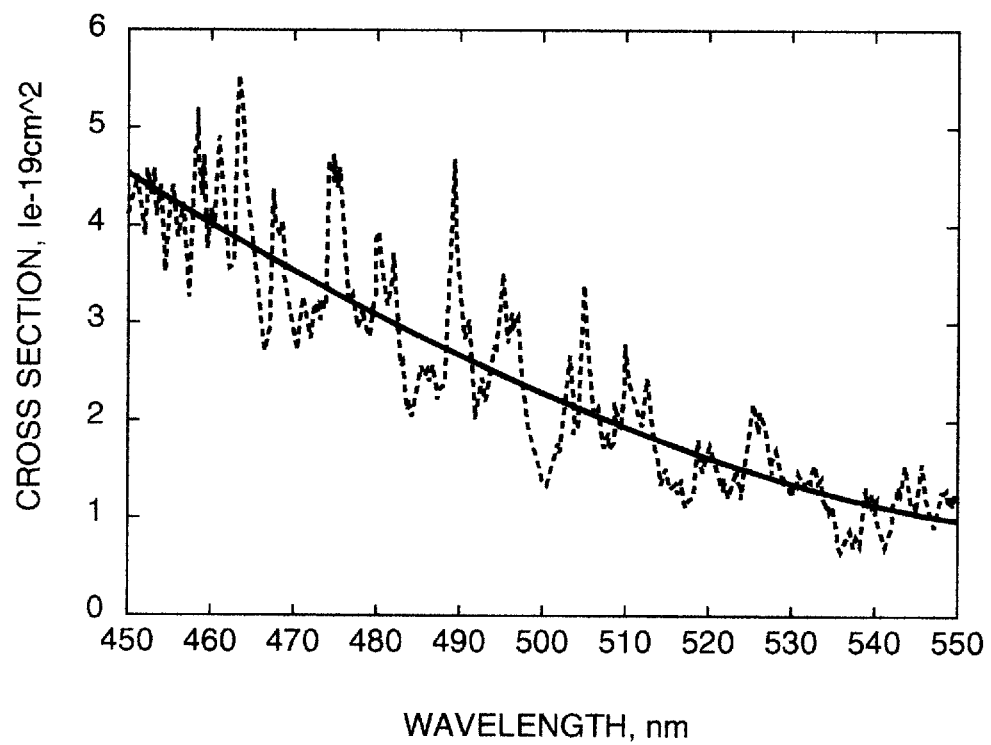
FIG. 1, discussed hereinabove, graphically depicts the visible light absorption spectrum of nitrogen dioxide.
Figure 2:
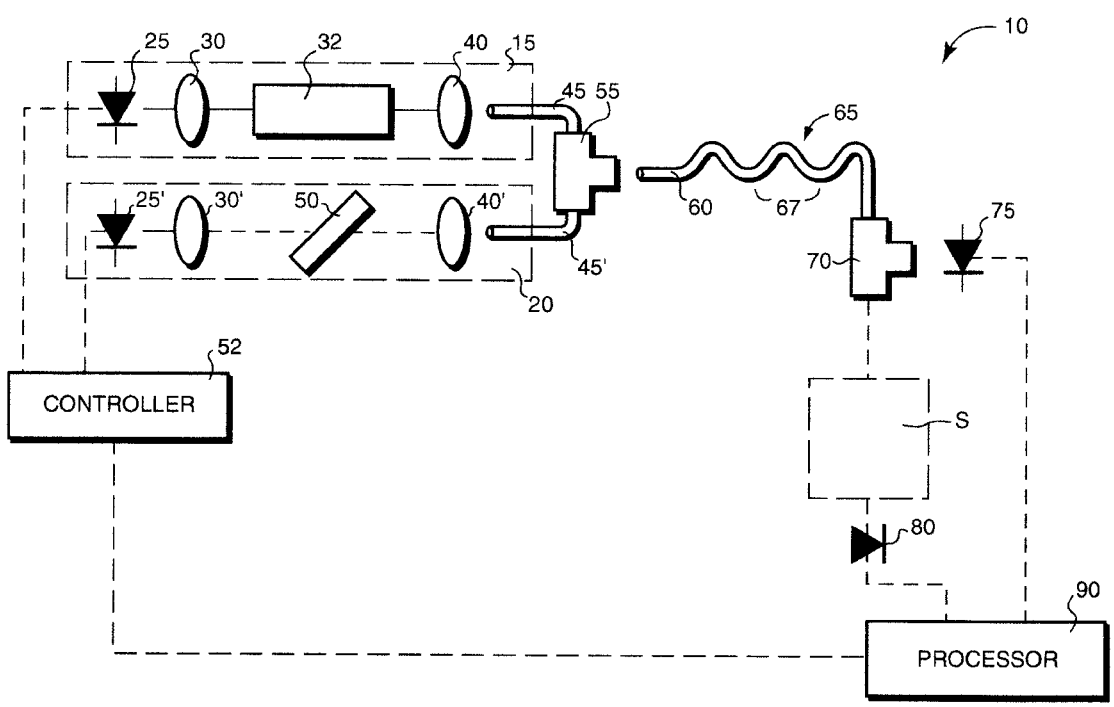
FIG. 2 schematically depicts a preferred embodiment of gas species detection according to the invention; and It will be appreciated that, for purposes of illustration, these figures are not necessarily drawn to scale.

FIG. 2 illustrates the detection of a gas species such as nitrogen dioxide or a halogen according to a preferred embodiment of the invention. An optical system generally designated at 10, includes first and second optical paths 15 and 20 in parallel. The first optical path 15 includes a light source 25 and a first lens 30 positioned to collimate light from the light source 25 into a correlation filter 32 comprising a cell containing the gas species. A second lens 40 is positioned to refocus light from the correlation filter 32 into an optical fiber 45. The second optical path 20 comprises a light source 25', lenses 30' and 40', an optical fiber 45' and a compensating filter 50 similarly configured. A controller 52 regulates operation of the first and second light sources 25 and 25'.

The optical fibers 45 and 45' are joined together by a directional coupler 55 to an output optical fiber 60 which includes a mode scrambler 65. An optical tap 70 couples a fraction of light in the optical fiber 60 to a first detector 75, hereinafter referred to as the reference detector. A second detector 80, hereinafter referred to as the analytical detector, receives the remainder of the light in the fiber 60 after it passes through a sample S in which a concentration of the gas species of interest is to be measured. A processor 90, coupled to the controller 52, receives signal from the reference detector 75 and the analytical detector 80.

In operation, the first and second light sources 25 and 25' are alternately energized by controller 52 to emit light which is focused by their respective first lenses 30 and 30' into their respective filters 32 and 50. The second lenses 40 and 40' focus light leaving the filters 32 and 50 into respective inputs of the directional coupler 55, which combines light from the filters 32 and 50 into the output optical fiber 60 so that when the first light source 25 is on, the fiber 60 receives light that has been processed by the correlation filter 32; and when the second light source 25' is on, the fiber 60 receives light that has been processed by the compensating filter 50.

Filtered light in the fiber 60 passes through the mode scrambler 65, which is a length of the fiber 60 having periodically placed bends 67. The bends 67 randomize the positions and distribution of angles of individual light rays with respect to the fiber axis and thus minimizes the effect of small variations in the geometry of the input, for example due to asymmetries in the directional coupler 55 or imperfections in the light sources and filters. Consequently, spatial variation of light intensity over the fiber cross section or angular variation in the propagation direction in the light supplied by the fiber 60 is suppressed. The scrambler 65 thus improves the uniformity of the light diverted by the optical tap 70 to the reference detector 75 and the light supplied to the sample S.

The reference detector 75 receives light intensity that is proportional to the intensity of light in the fiber 60. Synchronously with the alternate energizing of the light sources 25 and 25', the reference detector 75 produces a first reference signal corresponding to the intensity of the light that has traveled the first optical path 15 and a second reference signal corresponding to the intensity of the light that has traveled the second optical path 20. The controller 52 provides a constant current to the first light source 25 and operates the second light source 25' so as to minimize the difference between the first and second reference signals, thus providing equal power density to the sample S from the two filters 32 and 50.

The portion of the light in the fiber 60 not coupled to the reference detector passes to the sample S. The analytical detector 80 receives light transmitted through the sample S and, synchronously with the alternate energizing of the light sources 25 and 25', produces a first analytical signal, proportional to the intensity of light that has passed through the sample S after processing by the correlation filter 32, and a second analytical signal, proportional to the intensity of light that has passed through the sample S after processing by the compensating filter 50. The processor 90 derives the concentration of the gas species in the sample from the difference between the first and second analytical signals, normalized to their average value, using calibration data based on sample attributes—such as pressure, temperature, and length of optical path through the sample—as well as the properties of the correlation filter 32, compensating filter 50, and the light sources 25 and 25'. In a practical instrument, calibration for the effect of the properties of the filters and light sources is done by measuring the instrument's response to the gas species under standard conditions for several column densities within the intended operating range; while correction for the conditions under which the sample is actually observed would be based on a single generic calibration for a nominal set of filter and light source parameters.

For the purposes of this disclosure, the sample S is any expanse of space in which a gas concentration is to be determined. The sample S may contain a relatively static body of gas confined, for example, by a glass enclosure. Or, the sample may be a volume representative of a less-well-defined region, such as a large room or a portion of the earth's atmosphere.

The reference and analytical detectors are preferably photodiodes. The use of fiber optics is beneficial in that it minimizes the number of optical mountings and fixtures that must be used. Also, the fiber components are permanently adjustable so that subsequent alignment is not required. These features reduce the cost and enhance the reliability of the gas detector.

The light sources 25 and 25' may be incandescent lamps or gas discharge lamps. However, light-emitting diodes are preferred because of their stability, efficiency, lifetime, and response time. In the case of $NO_2$ detection, the light source preferably produces light in the 400-to-550 nm, blue-violet spectral region. Such LEDs are available commercially, made of either silicon carbide or indium-gallium nitride.

In general, the column density, equal to the product of the gas species concentration and the path length, chosen for the cell of correlation filter 32 reflects optimization between a too-high value—in which case the portions of the spectrum more strongly attenuated by the average absorption due to line overlap are not transmitted and the sample is probed only by the spectral portions having a weak average absorption—and a too-low value—which does not adequately remove the spectral lines, compromising sensitivity of the measurement. Pressure-dependent behavior of the particular gas species is also to be considered in design of the correlation filter. For example, in the case of $NO_2$ detection, one optimum correlation filter 32 cell design provides a path length of about 10 cm through a $NO_2$ pressure of about 20 Torr. A $NO_2$ pressure of this order, maintained at a sufficiently high temperature, minimizes the presence of the transparent dimeric form in the correlation filter 32. At 20 Torr and temperatures greater than 40° C., so little of the dimeric form is present that the invention may be used without correcting for small temperature fluctuations of the correlation filter 32.

The compensating filter 50 has an average transmission of the same form as that of the correlation filter 32 without the characteristic strong absorption at discrete wavelengths. In general, changing the filter thickness in the second optical path 20 changes the relative average transmission differently at different wavelengths. So, for a given filter material, the average transmission is tuned to a desired spectral profile by choice of the optical density of the filter. Thus, fixing the form of the average transmission's wavelength dependence also determines total transmission by the compensating filter, so that normally some mechanism for equalizing the intensity of light delivered to the sample S from the two filters 32 and 50 is desirable, such as the operation of the light sources 25 and 25' by the controller 52 based on the output of the reference detector 75.

As a practical matter, the compensating filter 50 is preferably configured so as to allow fine adjustment in situ of the optical density of the filter in the second optical path 20. For example, rotating a sheet of filter material about an axis perpendicular to the path 20 accomplishes such adjustment.

Modifying the path length of light through the filter in this way can correct the transmission-profile match between the compensating filter 50 and the correlation filter 32 for variables such as the pressure to which the correlation cell is filled and the absorption characteristics of the particular batch of material of which the compensating filter is made.

For $NO_2$ detection, the desired filter transmission properties are very similar to those of brown glass used for bottles. The average absorption cross-section of Schott glass type FG-13 agrees very closely with that of nitrogen dioxide, except for being slightly more absorptive at shorter wavelengths. Based on the nominal transmission of FG-13 glass, for the optimum correlation filter parameters described above, the desired FG-13 filter thickness is close to 1 mm. In practice, the FG-13 filter is rotated to provide an optical thickness of about 1.12 mm to the optical path 20. Although FG-13 is especially convenient for use in $NO_2$ detection, multilayer dielectric filters or a combination of dyed gelatin filters are suitable alternatives.

A $NO_2$ detector using a 10-cm, 20-Torr correlation cell and a 1-mm FG-13 compensating filter as described above, responds nearly linearly over sample column densities up to 2000 ppm-m. For example, a 10-cm sample column filled with pure nitrogen dioxide (with 1 Torr equivalent to 1316 ppm), the measurement shows a noise level of approximately 0.07 ppm-m when made using about 3 seconds averaging time per data point. Thus, for a two-meter path length through the sample, such an instrument is sensitive to sample concentrations from approximately 0.04 ppm to 1000 ppm. The minimum detectable concentration is subject to improvement by, for example, using a more efficient optical system or higher-output LEDs, or by averaging the measurements over a longer period of time. The upper end of the range is set by the degree of nonlinearity that is tolerable in the response.

Several variations of the foregoing system are encompassed by the GFCS-based, compensating-filter gas detection approach of the present invention. For example, with the incorporation of moving parts, a single light source may be used in a single optical path, into which filters 32 and 50 are alternately interposed. Or, rather than alternately energizing the two light sources 25 and 25', they may be left on, their light alternately supplied to their respective filters by synchronized mechanical choppers. Also, equalizing the light intensities reaching the sample S from the two optical paths 15 and 20 may be effected by including an attenuator in the second optical path 20 to adjust the intensity from the second path 20 to that from the first path 15 rather than by regulating operation of the second light source 25'. Congruity of the intensity leaving the two paths 15 and 20 may be implemented using a feedback loop receiving the reference signals or may be established using predetermined light source operation or attenuator parameters based on fixed properties of the two filters.

It will therefore be seen that the foregoing represents a highly advantageous approach to GFCS-based gas detection for broadband absorbers, especially nitrogen dioxide. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of determining a concentration of nitrogen dioxide in a sample, nitrogen dioxide having a transmission spectrum defined by at least one absorption line and an average broadband transmission varying according to a wavelength dependence, the method comprising the steps of:

a. providing in a first optical path a correlation filter, comprising a first cell for containing nitrogen dioxide at a correlation filter pressure;

b. providing in a second optical path a compensating filter, having an average broadband transmission that varies according to the wavelength dependence without the at least one absorption line;

c. supplying light from a first light source to the correlation filter;

d. supplying light from a second light source to the compensating filter;

e. merging light that has passed through the correlation filter and light that has passed through the compensating filter in a combined optical path;

f. measuring light in the combined optical path;

g. supplying light from the combined path to the sample; and h. measuring light leaving the sample.

2. The method of claim 1 wherein:

a. the first and second light sources are alternately energized so as to supply light alternately to the correlation filter and to the compensating filter;

b. light is measured in the combined optical path synchronously with the alternate energizing so as to produce first and second reference signals corresponding to intensities of light that have passed respectively through the correlation filter and the compensating filter;

c. light leaving the sample is measured synchronously with the alternate energizing of the light sources, thereby producing first and second analytical signals corresponding to intensities of light that has passed through the sample respectively after passing through the correlation filter and after passing through the compensating filter, a difference between the first and second analytical signals indicating the concentration; and further comprising the step of regulating operation of the second light source based on a difference between the first and second reference signals.

3. The method of claim 1 wherein the two light sources are two light-emitting diodes that emit light having a wavelength in the range of 400 nm to 550 nm.

4. The method of claim 1 wherein the compensating filter is of FG-13 glass.

5. The method of claim 1 wherein the compensating filter comprises a second cell containing nitrogen dioxide at a compensating filter pressure substantially identical to the correlation filter pressure, the second cell being located in a constant magnetic field having strength greater than approximately 1,000 Gauss.

6. The method of claim 1 further comprising the step of oxidizing any nitric oxide in the sample to nitrogen dioxide, the indicated concentration of nitrogen dioxide denoting a total concentration of nitric oxide and nitrogen dioxide.

7. The method of claim 6 wherein the step of oxidizing comprises supplying ozone to the sample.

8. The method of claim 1 further comprising the step of calculating a temperature based on the indicated concentration of nitrogen dioxide.

9. The method of claim 8 wherein the sample contains nitrogen dioxide at a pressure in the approximate range 40 to 100 Torr.

10. A method of determining a concentration of a gas species in a sample, the gas species having a transmission spectrum defined by at least one absorption line and an average broadband transmission varying according to a wavelength dependence, the method comprising the steps of:
   a. filtering light alternately through a correlation filter comprising a first cell containing the gas species at a correlation filter pressure, thereby creating correlation-filtered light having a correlation-filtered intensity, and a compensating filter, thereby creating compensating-filtered light having a compensating-filtered intensity, the compensating filter having an average broadband transmission that varies according to the wavelength dependence without the at least one absorption line;
   b. alternately passing into the sample compensating-filtered light and correlation-filtered light;
   c. detecting light leaving the sample so as to alternately produce a first analytical signal proportional to an intensity of correlation-filtered light that has passed through the sample and a second analytical signal proportional to an intensity of compensating-filtered light that has passed through the sample; and
   d. deriving the concentration of the gas species based on the difference between the first and second signals.

11. The method of claim 10 wherein the step of alternately filtering comprises alternately passing light from a first of two light sources into the correlation filter and light from a second of the two light sources into the compensating filter, the first and second light sources being substantially identical.

12. The method of claim 11 further comprising the step of making the compensating-filtered light intensity and the correlation-filtered light intensity the same by controlling operation of the second of the two light sources based on a difference between the compensating-filtered light intensity and the correlation-filtered light intensity.

13. The method of claim 12 further comprising the step of alternately producing, synchronously with the alternate passing, a first reference signal proportional to the correlation-filtered intensity and a second reference signal proportional to the compensating-filtered intensity.

14. The method of claim 11 wherein the step of detecting light leaving the sample so as to generate first and second analytical signals is performed synchronously with the alternate passing of light to the respective filters.

15. The method of claim 11 wherein alternately passing light from each of the two light sources into the respective filters comprises alternately energizing the two light sources.

16. The method of claim 10 wherein the compensating filter consists of colored glass having thickness and composition chosen so that the average transmission of the compensating filter varies according to the wavelength dependence.

17. The method of claim 10 wherein the compensating filter passes the at least one absorption line.

18. The method of claim 10 wherein the gas species is nitrogen dioxide.

19. The method of claim 18 wherein the two light sources are light-emitting diodes that emit light having a wavelength in the range of 400 nm to 550 nm.

20. The method of claim 18 wherein the compensating filter comprises a second cell containing nitrogen dioxide at a compensating filter pressure substantially identical to the correlation filter pressure, the second cell being located in a constant magnetic field having strength greater than approximately 1,000 Gauss.

21. The method of claim 18 wherein the compensating filter is made of FG-13 glass.

22. The method of claim 18 further comprising the step of oxidizing any nitric oxide in the sample to nitrogen dioxide, the derived concentration of nitrogen dioxide indicating a total concentration of nitric oxide and nitrogen dioxide.

23. The method of claim 22 wherein the step of oxidizing comprises supplying ozone to the sample.

24. The method of claim 18 further comprising the step of calculating a temperature based on the derived concentration of nitrogen dioxide.

25. An apparatus for determining a concentration of nitrogen dioxide in a sample, nitrogen dioxide having a transmission spectrum defined by at least one absorption line and an average broadband transmission varying according to a wavelength dependence, the apparatus comprising:
   a. a correlation filter, in a first optical path, comprising a first cell for containing nitrogen dioxide at a correlation filter pressure;
   b. a compensating filter, having an average broadband transmission that varies according to the wavelength dependence without the at least one absorption line, in a second optical path;
   c. a light generator comprising a first light source for supplying light to the correlation filter and a second light source for supplying light to the compensating filter;
   d. combining means for merging light that has passed through the correlation filter and the compensating filter in a combined optical path, the combined path supplying light to the sample;
   e. a reference detector for measuring light in the combined optical path; and
   f. an analytical detector for measuring light leaving the sample.

26. The apparatus of claim 25 wherein the light generator comprises a controller for alternately energizing the first and second light sources so as to alternately supply light to the correlation filter and the compensating filter,
   a. the reference detector being configured to measure light synchronously with the alternate energizing so as to produce first and second reference signals corresponding to intensities of light that have passed respectively through the correlation filter and the compensating filter;
   b. the controller regulating operation of the second light source based on a difference between the first and second reference signals;
   the analytical detector being configured to measure light leaving the sample synchronously with the alternate energizing of the light sources, thereby producing first and second analytical signals corresponding to intensities of light that has passed through the sample respectively after passing through the correlation filter and after passing through the compensating filter; and
   c. a difference between the first and second analytical signals indicating the concentration.

27. The apparatus of claim 26 wherein the two light sources are light-emitting diodes that emit light having a wavelength in the range of 400 nm to 550 nm.

28. The apparatus of claim 27 wherein the compensating filter is FG-13 glass.

29. The apparatus of claim 26 wherein the compensating filter comprises a second cell containing nitrogen dioxide at a compensating filter pressure substantially identical to the correlation filter pressure, the second cell being located in a constant magnetic field having strength greater than approximately 1,000 Gauss.

30. The apparatus of claim 26 further comprising a system for oxidizing any nitric oxide in the sample to nitrogen dioxide, the indicated concentration of nitrogen dioxide denoting a total concentration of nitric oxide and nitrogen dioxide.

31. The apparatus of claim 30 wherein the system for oxidizing comprises an ozone generator.

32. The apparatus of claim 26 wherein the sample contains nitrogen dioxide at a pressure in the approximate range 40 to 100 Torr, the indicated concentration of nitrogen dioxide denoting a temperature.

33. An apparatus for determining a concentration of a gas species in a sample, the gas species having a transmission spectrum defined by at least one absorption line and an average broadband transmission varying according to a wavelength dependence, the apparatus comprising:

a. a correlation filter comprising a first cell for containing the gas species at a correlation filter pressure;

b. a compensating filter having an average broadband transmission that varies according to the wavelength dependence without the at least one absorption line;

c. a light generator;

d. means for supplying light alternately to the correlation filter and the compensating filter;

e. means for passing light, alternately from the correlation filter and the compensating filter, to the sample;

f. an analytical detector for alternately producing a first analytical signal proportional to the intensity of light that has passed through the sample from the correlation filter and a second analytical signal proportional to light that has passed through the sample from the compensating filter; and g. means for evaluating the concentration based on the difference between the first and second analytical signals.

34. The apparatus of claim 33 further comprising a reference detector for alternately producing a first reference signal proportional to a light intensity leaving the correlation filter and a second reference signal proportional to a light intensity leaving the compensating filter.

35. The apparatus of claim 34 wherein the light generator comprises a controller operable to regulate operation of the generator, based on the difference between the first and second reference signals, so that the intensity of light leaving the correlation filter and the intensity of light leaving the compensating filter are the same.

36. The apparatus of claim 33 wherein the light generator comprises two substantially identical light sources, the means for alternately supplying light alternately directing light from a first light source to the correlation filter and directing light from a second light source to the compensating filter.

37. The apparatus of claim 36 further comprising a reference detector for alternately producing, synchronously with the alternate directing of light from the two light sources, a first reference signal proportional to a light intensity leaving the correlation filter and a second reference signal proportional to a light intensity light leaving the compensating filter, the light generator comprising a controller operable to regulate operation of the generator, based on the difference between the first and second reference signals, so that the intensity of light leaving the correlation filter and the intensity of light leaving the compensating filter are the same.

38. The apparatus of claim 36 wherein the analytical detector is configured to produce the first and second analytical signals synchronously with the alternate supplying of light to the correlation filter and the compensating filter.

39. The apparatus of claim 36 wherein the means for alternately supplying light alternately energizes the two light sources.

40. The apparatus of claim 36 wherein the two light sources are two light-emitting diodes.

41. The apparatus of claim 33 wherein the compensating filter consists of colored glass having thickness and composition chosen so that the average transmission of the compensating filter varies according to the wavelength dependence.

42. The apparatus of claim 33 wherein the compensating filter passes the at least one absorption line.

43. The apparatus of claim 33 wherein the gas species is nitrogen dioxide.

44. The apparatus of claim 43 wherein the two light sources are light-emitting diodes that emit light having a wavelength in the range of 400 nm to 550 nm.

45. The apparatus of claim 43 wherein the compensating filter comprises a second cell containing nitrogen dioxide at a compensating filter pressure substantially identical to the correlation filter pressure, the second cell being located in a constant magnetic field having strength greater than approximately 1,000 Gauss.

46. The apparatus of claim 43 wherein the compensating filter is made of FG-13 glass.

47. The apparatus of claim 43 further comprising a system for oxidizing any nitric oxide in the sample to nitrogen dioxide, the evaluated concentration of nitrogen dioxide indicating a total concentration of nitric oxide and nitrogen dioxide.

48. The apparatus of claim 47 wherein the system for oxidizing comprises an ozone generator.

49. The apparatus of claim 43 wherein the sample contains nitrogen dioxide at a pressure in the approximate range 40 to 100 Torr, the evaluated concentration of nitrogen dioxide indicating a temperature.

* * * * *